(12) United States Patent
Kang et al.

(10) Patent No.: US 7,964,393 B2
(45) Date of Patent: Jun. 21, 2011

(54) CONSTITUTIVE PROMOTER LIP3

(75) Inventors: Sang-Ho Kang, Suwon-si (KR); Teresa Lee, Suwon-si (KR); Young-Mi Kim, Suwon-si (KR); Sun-Hwa Ha, Suwon-si (KR); Seok-Cheol Suh, Hwaseong-si (KR)

(73) Assignee: Korean Rural Development Administration, Suwon-si (KR)

( * ) Notice: Subject to any disclaimer, the term of this patent is extended or adjusted under 35 U.S.C. 154(b) by 0 days.

(21) Appl. No.: 12/502,849

(22) Filed: Jul. 14, 2009

(65) Prior Publication Data

US 2010/0005540 A1    Jan. 7, 2010

(30) Foreign Application Priority Data

Nov. 3, 2008   (KR) .................... 10-2008-0108451

(51) Int. Cl.
  *A01H 1/00*   (2006.01)
  *C12N 15/29*  (2006.01)
  *C07H 21/04*  (2006.01)
  *C07K 14/415* (2006.01)

(52) U.S. Cl. ........ 435/320.1; 435/6; 435/69.1; 435/468; 435/419; 530/370; 536/24.1; 800/278; 800/295

(58) Field of Classification Search ............. 435/6, 69.1, 435/468, 419, 320.1; 536/24.1; 800/278, 800/295; 530/370
See application file for complete search history.

(56) References Cited

U.S. PATENT DOCUMENTS

2007/0056055 A1*   3/2007   Budworth et al. ............ 800/278

OTHER PUBLICATIONS

Chao et al. (GenEmbl Database, Acc. No. AC007508, direct submission, Oct. 11, 2000, see Result 1.*

* cited by examiner

*Primary Examiner* — Phuong T Bui
(74) *Attorney, Agent, or Firm* — Joseph Hyosuk Kim; JHK Law

(57) ABSTRACT

The present invention relates to a novel constitutive promoter of plant, particularly to a putative lipase promoter Lip3 derived from *Arabidopsis*, a method for isolating the same, a recombinant expression vector containing the same and a use of the same for improving traits of a farm product. The constitutive promoter of the present invention can be applied to induce a constitutive gene expression such as herbicide resistance gene and reporter gene, because it can express a foreign gene regardless of its expression site. In addition, it can be widely used to develop a transgenic plant improving its useful trait.

5 Claims, 3 Drawing Sheets

SEQUENCE LISTING

```
<160> NUMBER OF SEQ ID NOS: 13

<210> SEQ ID NO 1
<211> LENGTH: 1981
<212> TYPE: DNA
<213> ORGANISM: Artificial Sequence
<220> FEATURE:
<223> OTHER INFORMATION: Arabidopsis thaliana

<400> SEQUENCE: 1
```

```
taaggaagtt gaagagctgg taccgtttgt gatcgctact atttcttctg caatcacggt      60
aaacattctt gatcagccag ttccgggaat gactaaaaca tatttgtatc tacgctgata     120
attagttttgg taagaaaaaa cacatgtaca tgttacgttg ttttgaaact gaatgttgaa    180
ttcaggaatt ggtttgcatg ggaggaagaa cattcctagt tcctggaaat ttcccgatcg     240
gatactcagc atcctatttg acattataca aaacatcaaa caaggaagag tatgatcctc     300
taacaggatg tttgaaatgg cttaacgatt tctcagaata ctacaataag cagcttcagg     360
aagaactcaa cggactcagg aagttgtacc ctcatgtcaa catcatatat gctgattact     420
acaacgcttt gttgcgcctt ttccaagaac cagccaaatt cggttaggct tcttgaatcc     480
tccaagagat ttcttcacaa ccaagtcact catttgattc actaattaat taaccgattt     540
tattatccaa tcagggttta tgaacagacc cttgcccgct tgttgcggtg taggaggatc     600
ttacaacttc aactttagta gaagatgtgg gagtgtagga gttgaatact gcgatgatcc     660
ttcacagtat gtgaattatg atggcattca tatgacggag gcggcataca gattgatatc     720
tgagggctta ctcaagggac cgtatgctat tcctcctttc aagtggtctt gcctcagctc     780
cgagattatg aataagatgt cattagatac tcagattctt gatgaacagc tactacaagg     840
ttgtctgaaa gtttgagaga caagagaaag agtggaaaaa acatataggt tcttaagtgt     900
ttgtgtcttc ttcttttttg ttccgggtaa cggtgttaat tagccttagg tgcatcatgc     960
atgtgttgga tcatgtatta tctttgtatt gtattgtttt cgttagtttg ggtaagagtt    1020
agtatcctta attgttggac catgtacact gtcatatata atttaactat atacaaaaca    1080
attaaatgca taatttacgc atcgcgtggc caaatttcta gaatcaaata tggttttatg    1140
gtaagaaatc agaacactat gtaaatttga ttaacgatgg gactaattca gaaaaataaa    1200
taaatactaa gtctaaagaa atagttggga actggcggaa aaaaaaagt tggagagtct     1260
ttaggtctaa acacatgtta catgtataaa aggaatttaa caaggttgta tacgtagtta    1320
cgtacattag gtgtttctct gttcgtgtgt acaaccgcat attttttaatc tttggatcat   1380
atagtgttga tgaatgtgta catcaactat tggagatata atgtattatg ctgtatacgt    1440
acaacagaat gttccaaaaa tctttcttct tttttttatt ttatttttaaa tcggccccaa    1500
tggtgctata ataaacgaga aagccaaaaa tactacaaat aaaagcctca gtgatgggtt    1560
tatcgtttaa gcgaaagtga cgaaagagag gaaactagac agatacgaca gtaagttttg    1620
gtcatcgaag atacgtattg ggatccgctc acaagaattt gttgtgtgtc ttttttgctaa   1680
aaggccaata cgaaaatcgt tgataattcg tttcatctac cgcaatcact ttatccttga    1740
ccaaaaaaag aaagaaataa ctcaaatatc aattttataa tcaaataaaa acttaaataa    1800
tcaaccaata tacccgtgtg tgtcaaacca tactgcatcc caataattga tcttttaatc    1860
attctttatt atcttatcct tggtattgtg gctagtgggg tattttcaaa agacttttt    1920
gacaaatcaa catcacacta ttaaaaaagg gatctcgacg gagaccaacc ttcagctctc    1980
t                                                                    1981
```

<210> SEQ ID NO 2
<211> LENGTH: 24
<212> TYPE: DNA
<213> ORGANISM: Artificial Sequence
<220> FEATURE:
<223> OTHER INFORMATION: Arabidopsis thaliana

<400> SEQUENCE: 2
ccgtaggtag gaaatgtggg actg       24

<210> SEQ ID NO 3
<211> LENGTH: 28
<212> TYPE: DNA
<213> ORGANISM: Artificial Sequence
<220> FEATURE:
<223> OTHER INFORMATION: Arabidopsis thaliana

<400> SEQUENCE: 3
atgaacatga tccaagacaa tactaagg                                      28

<210> SEQ ID NO 4
<211> LENGTH: 25
<212> TYPE: DNA
<213> ORGANISM: Artificial Sequence
<220> FEATURE:
<223> OTHER INFORMATION: Arabidopsis thaliana

<400> SEQUENCE: 4
gtttcacatt aacattgtgg tcatt                                         25

<210> SEQ ID NO 5
<211> LENGTH: 24
<212> TYPE: DNA
<213> ORGANISM: Artificial Sequence
<220> FEATURE:
<223> OTHER INFORMATION: Arabidopsis thaliana

<400> SEQUENCE: 5
gaggtaccag taatcatgtt cttg                                          24

<210> SEQ ID NO 6
<211> LENGTH: 32
<212> TYPE: DNA
<213> ORGANISM: Artificial Sequence
<220> FEATURE:
<223> OTHER INFORMATION: Arabidopsis thaliana

<400> SEQUENCE: 6
aaaaagcagg cttaaggaag ttgaagagct gg                                 32

<210> SEQ ID NO 7
<211> LENGTH: 32
<212> TYPE: DNA
<213> ORGANISM: Artificial Sequence
<220> FEATURE:
<223> OTHER INFORMATION: Arabidopsis thaliana

<400> SEQUENCE: 7
agaaagctgg gtagagagct gaaggttggt ct                                 32

<210> SEQ ID NO 8
<211> LENGTH: 29
<212> TYPE: DNA
<213> ORGANISM: Artificial Sequence
<220> FEATURE:
<223> OTHER INFORMATION: Arabidopsis thaliana

<400> SEQUENCE: 8
aaaaagcagg ctggtcccca gattagcct                                     29

<210> SEQ ID NO 9
<211> LENGTH: 29
<212> TYPE: DNA
<213> ORGANISM: Artificial Sequence
<220> FEATURE:
<223> OTHER INFORMATION: Arabidopsis thaliana

```
<400> SEQUENCE: 9
agaaagctgg gtcccgggga tcctctaga                                              29

<210> SEQ ID NO 10
<211> LENGTH: 29
<212> TYPE: DNA
<213> ORGANISM: Artificial Sequence
<220> FEATURE:
<223> OTHER INFORMATION: Arabidopsis thaliana

<400> SEQUENCE: 10
ggggacaagt ttgtacaaaa aagcaggct                                              29

<210> SEQ ID NO 11
<211> LENGTH: 29
<212> TYPE: DNA
<213> ORGANISM: Artificial Sequence
<220> FEATURE:
<223> OTHER INFORMATION: Arabidopsis thaliana

<400> SEQUENCE: 11
ggggaccact ttgtacaaga aagctgggt                                              29

<210> SEQ ID NO 12
<211> LENGTH: 24
<212> TYPE: DNA
<213> ORGANISM: Artificial Sequence
<220> FEATURE:
<223> OTHER INFORMATION: Arabidopsis thaliana

<400> SEQUENCE: 12
acctgcgtca atgtaatgtt ctgc                                                   24

<210> SEQ ID NO 13
<211> LENGTH: 20
<212> TYPE: DNA
<213> ORGANISM: Artificial Sequence
<220> FEATURE:
<223> OTHER INFORMATION: Arabidopsis thaliana

<400> SEQUENCE: 13
ctccctgctg cggtttttca                                                        20
```

CONSTITUTIVE PROMOTER LIP3

BACKGROUND OF THE INVENTION

1. Field of the Invention

The present invention relates to a novel constitutive promoter of plant, particularly to a putative lipase promoter Lip3 derived from *Arabidopsis*, a method for isolating the same, a recombinant expression vector containing the same and uses of the same for improving traits of a farm product. The constitutive promoter of the present invention can be applied to induce a constitutive gene expression such as herbicide resistance gene and reporter gene, because it can express foreign gene regardless of its expression site. In addition, it can be widely used to develop a transgenic plant improving its useful trait.

2. Background of the Related Art

Promoters that are commonly used to express plant genes constitutively or tissue-specifically aiming at transformation should be classified according to their function as follows.

First, there are promoters inducing a constitutive gene expression. One constitutive promoter suitable in a plant may be 35S RNA gene promoter that is derived from cauliflower mosaic virus (CaMV) and being utilized for main promoter of dicotyledons. In addition, actin promoter of rice plant and ubiquitin promoters of corn are commonly used for constitutive promoter suitable in monocotyledons. Recently, cytochrome C (OsOc1) promoter of rice plant is also developed by domestic researchers and being utilized (Korean Patent Registration NO. 10-0429335). These constitutive promoters are mostly introduced into basic vectors for plant transformation so as to promote the expression of antibiotic resistance genes, herbicide resistance genes and reporter genes for selective marker. Therefore, they are considered with first priority to elucidate the function of target gene within a plant in the research aspect.

Second, there are seed-specific promoters. One seed-specific promoter may be a major storage protein promoter of rice plant. In practice, glutelin promoter of rice plant has been used to develop golden rice and being widely applied to induce the seed-specific expression of monocotyledons. In addition, the seed-specific promoters inducing the gene expression of dicotyledons may be lectin promoter derived from peas, napin promoter derived from cabbage, DC-3 promoter derived from carrots and the like. This DC-3 promoter is applied to increasingly produce vitamin E by inducing the gene expression of γ-tocopherol methyl transferase (γ-TMT) in *Arabidopsis* seeds. Besides, oleosin promoter derived from green *perilla* is tried to promote the seed-specific expression and already applied for a patent (Korean Patent Application NO. 10-2006-0000783). These seed-specific promoters become a valuable tool to accumulate useful proteins and to produce useful substance from farm plants applicable for seed crops or seed food in itself and raw material of food.

Third, there are specific promoters expressing in roots. The root-specific promoter has not been commercialized yet. However, peroxidase (prxEa) derived from *Arabidopsis* is separated and identified to be expressed specifically in a root. In addition, several promoters are recently reported to be related with the root-specific expression, after being isolated from mads gene derived from sweet potatoes (ibMADS) and glucose-inducible ADP-glucose pyrophosphatase (AGPase). Furthermore, these promoters are confirmed to promote transient gene expressions root-specifically in carrots and radishes and already registered with patents (Korean Patent Registration NO. 10-0604186 and Korean Patent Registration NO. 10-0604191). Therefore, it is expected that the root-specific promoters should be utilized to accumulate useful proteins and to produce useful substance from root plants applicable for farm crops or food in itself and raw material of food.

Fourth, there are specific promoters for other tissues such as leaves. The tissue-specific promoter may include ribulose bisphosphate carboxylase/oxygenase small subunit (rbcS) promoter that is derived from a rice plant and corn and strongly induces a gene expression exclusively in a photosynthetic tissue such as leaves, RolD promoter that is derived from *Agrobacterium* and induces a root-specific expression in a plant, patatin promoter that is derived from a potato and induces a tuber-specific expression, phytoene synthase (PDS) promoter that is derived from a tomato and induces a fruit-specific expression in a mature plant, and oleocin promoter that is derived from cabbage and identified to promote a pollen-specific expression in cabbage flowers. The present inventors also have been attempted to induce the gene expression of cytotoxic Bt protein by using a tapetum-specific BcA9 promoter. Then, we have developed a male-sterile plant and registered a patent (Korean Patent Registration No. 10-0435143).

As illustrated above, a lot of promoters have been discovered from various tissues of plants and reported to accomplish their purpose. Presently, they are being investigated and developed industrially. However, most of universal promoters already commercialized or applied by plant researchers may just belong to the above-mentioned cases. Therefore, it is required in the future to actively develop novel promoters controlling gene expressions more accurately according to the developer's intention.

In order to settle above-mentioned problems, the present inventors have tried to exploit novel constitutive promoters of plant. As a consequence, a lipase promoter Lip3 derived from *Arabidopsis* has been identified to constitutively express an exogenous gene. Then, the Lip3 promoter region was amplified by using a oligonucleotide primer set of SEQ. ID. NO: 6 and SEQ. ID. NO: 7. Furthermore, recombinant expression vectors containing the promoter have been constructed and transformed to *Arabidopsis* plant. The resulting *Arabidopsis* has been investigated to measure a degree of constitutive expression with histochemical staining and fluorometric assay of GUS activity, GUS transcripts and the like. Therefore, it is confirmed that the constitutive promoter of the present invention should induce a constitutive expression regardless of its expression site. Hence, the present invention has been completed successfully.

SUMMARY OF THE INVENTION

The object of the present invention is to provide a novel constitutive promoter of plant, a method for preparing the same and uses of the same for improving traits of a farm product.

In order to accomplish the above-mentioned object, the present invention provides a constitutive promoter Lip3 of plant containing a part of or whole nucleotide sequence of SEQ. ID. NO: 1.

In addition, the present invention provides the recombinant expression vector containing the constitutive promoter of plant pBGWFS7-PAtLip3 (accession number: KACC 95086P). The strains have been redeposited with International Deposit Organization, the Korean Collection for Type Cultures (KCTC) of the Republic of Korea on Jun. 19, 2009, and identified as KCTC accession numbers, KCTC 11522 BP.

In addition, the present invention provides a method for preparing the constitutive promoter Lip3 of plant, which is obtained by performing a polymerase chain reaction with oligonucleotide primers of SEQ. ID. NO: 6 and SEQ. ID. NO: 7.

In addition, the present invention provides a method for expressing a target protein constitutively within a plant, which comprises steps: (1) constructing a plant expression vector expressing foreign gene by using the constitutive promoter; (2) transforming a plant vehicle with the plant expression vector; and (3) introducing the plant vehicle into a plant to express foreign gene.

Additional advantages, objects and features of the present invention will be set forth in part in the description which follows and in part will become apparent to those having ordinary skill in the art upon examination of the following or may be learned from practice of the invention.

It is natural that other objects and advantages of the invention may be realized and attained by the structure particularly pointed out in the written description and claims hereof as well as the appended drawings.

BRIEF DESCRIPTION OF THE DRAWINGS

The above and other objects, features and other advantages of the present invention will be more clearly understood from the following detailed description taken in conjunction with the accompanying drawings, in which.

M: 1 Kb plus DNA ladder marker; AtLip3: lipase gene of *Arabidopsis*; Co10: non-transformed *Arabidopsis*; and EF1α: elongation factor 1α gene of *Arabidopsis*.

Figure 2:
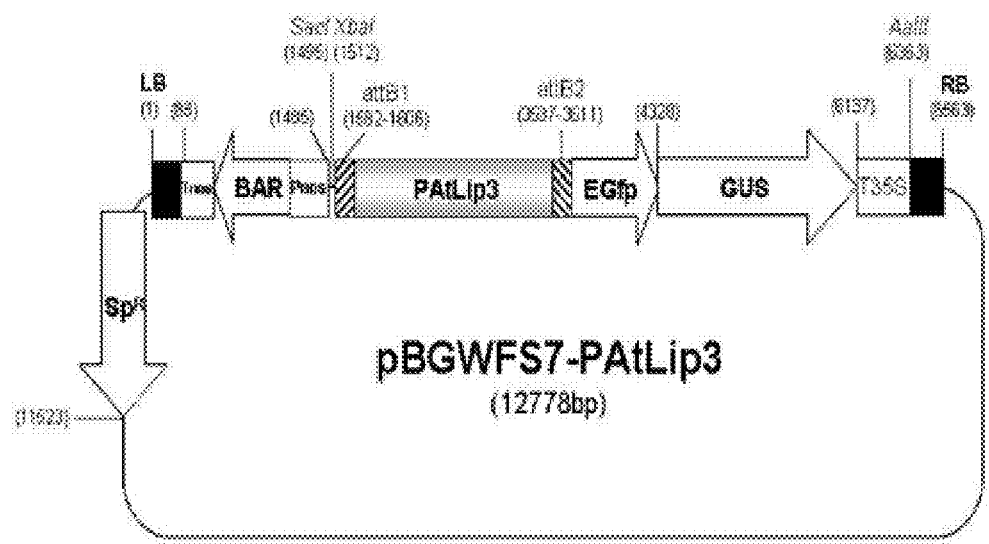

FIG. 2 depicts a construction map of the plant expression vector pBGWFS7-PAtLip3.

LB: left border; Tnos: nos terminator; BAR: herbicide resistance gene; Pnos: nos promoter; PAtLip3: lipase promoter; P35S: Cauliflower mosaic virus 35S promoter; Egfp: green fluorescent protein gene; GUS: blue-coloring β-glucuronidase gene; T35S: Cauliflower mosaic virus 35S terminator; and RB: right border.

Figure 3:
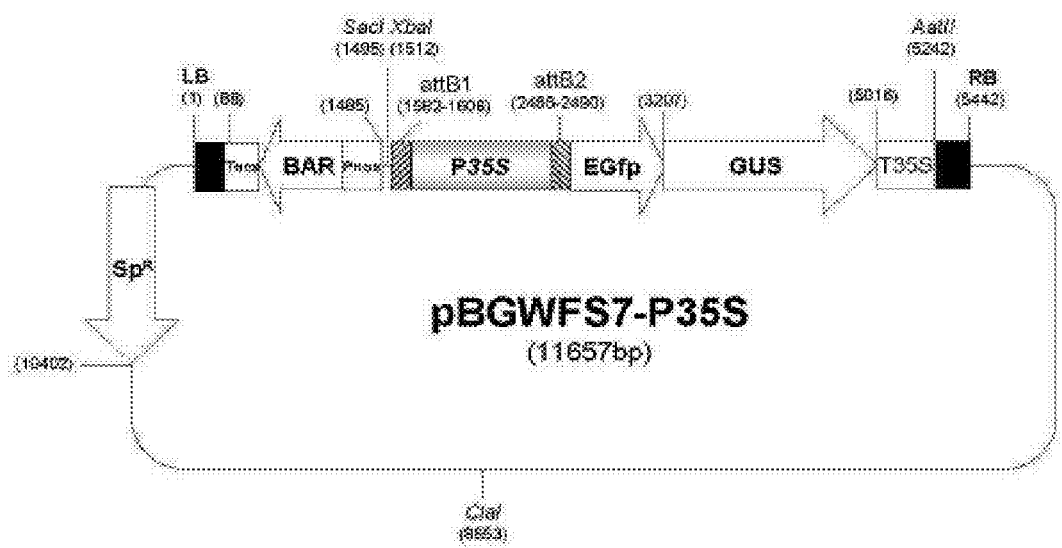

FIG. 3 depicts a construction map of the plant expression vector pBGWFS7-P35S as a control group.

Figure 4:
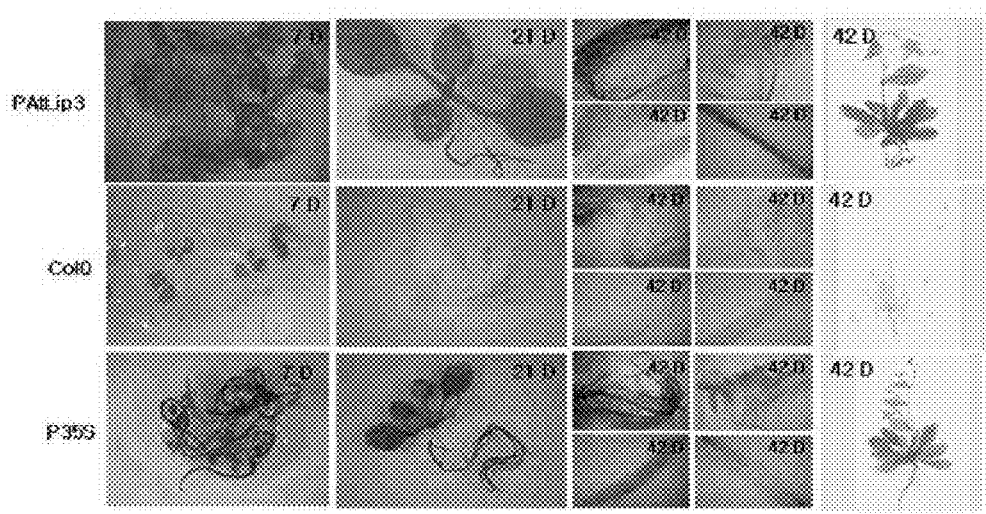

FIG. 4 depicts the *Arabidopsis* plant transformed—with the plant expression vector pBGWFS7-PAtLip3 that appears histochemical staining of GUS activity while growing from seedling to maturing plant.

Co10: non-transformed *Arabidopsis*; P35S::GUS: transgenic *Arabidopsis* as a control group; PAtLip3::GUS: *Arabidopsis* transformed with the plant expression vector pBGWFS7-PAtLip3; 7D: 7-day-old *Arabidopsis* seedlings; 21D: 21-day-old *Arabidopsis* plant; and 42D: 42-day-old *Arabidopsis* plants.

Figure 5:
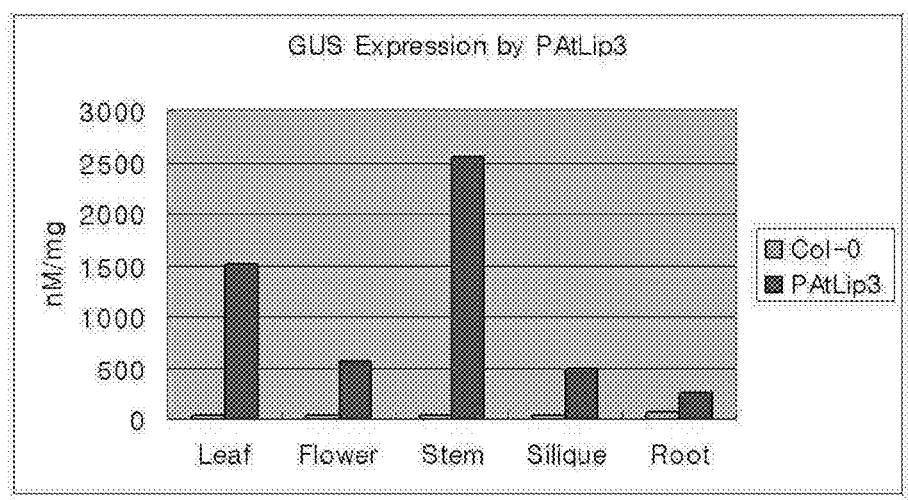

FIG. 5 depicts a quantitative fluorometric GUS assay of transgenic *Arabidopsis* expressed GUS from the AtLip3 promoter of the present invention, compared with a positive control group.

Figure 6:

FIG. 6 depicts the promoter gene of the present invention that is amplified by using total RNAs with specific primers after being separated respectively from root, leaf, stem, flower and silique tissues of *Arabidopsis* transformed with the plant expression vector pBGWFS7-PAtLip3, compared with a positive control group and GUS gene.

DETAILED DESCRIPTION OF THE PREFERRED EMBODIMENT

Hereinafter, the present invention will be described more clearly as follows.

The present invention provides a putative lipase gene promoter for plant constitutive promoter.

Particularly, the constitutive promoter Lip3 of plant containing a part of or whole nucleotide sequences of SEQ. ID. NO: 1 is provided. The constitutive promoter of plant may include all constitutive promoters derived from *Arabidopsis* sp., but may be a constitutive promoter derived from *Arabidopsis thaliana* preferably.

This constitutive promoter is a novel gene promoter not elucidated in its function yet and may correspond to an upstream 1,981 bp sequence of coding region in the putative lipase gene. The nucleotide sequence of SEQ. ID. NO: 1 may contain one or more modified sequences that are substituted, deleted or added partially, but should have more than 90% of sequence homology preferably.

In addition, the present invention provides a pair of primers that is comprised of oligonucleotides of SEQ. ID. NO: 6 and SEQ. ID. NO: 7 and used to amplify the constitutive promoter. The primers are composed of a forward primer and a reverse primer having 32 bp respectively in order to amplify the constitutive promoter Lip3 specifically. The primers may be manufactured by a synthetic procedure of oligonucleotides already disclosed in prior arts. Otherwise, they may be purchased after being commercially synthesized. The primers may contain one or more modified nucleotides partially within a certain nucleotide sequence. The nucleotide sequences modified above may be nucleotide sequences substantially similar to the nucleotide sequences that are prepared by performing a polymerase chain reaction (PCR) with the non-modified primers of SEQ. ID. NO: 6 and SEQ. ID. NO: 7, even though being deleted, substituted or added.

In addition, the present invention provides a method for preparing the constitutive promoter Lip3 of plant, which is obtained by performing a polymerase chain reaction with oligonucleotide primers of SEQ. ID. NO: 6 and SEQ. ID. NO: 7.

In addition, the present invention provides a recombinant expression vector containing the constitutive promoter. Particularly, the recombinant expression vector pBGWFS7-PAtLip3 containing the constitutive promoter of SEQ. ID. NO: 1 is provided.

The recombinant expression vector pBGWFS7-PAtLip3 has been deposited to National Institute of Agricultural Biotechnology Genebank, an International Deposit Organization (accession number: KACC 95086P, KCTC 11522 BP).

The recombinant expression vector may contain one or more herbicide resistance genes and/or reporter genes, in addition to the constitutive promoter of SEQ. ID. NO: 1. The herbicide resistance gene may be BAR gene and the like and the reporter gene may be Egfp:gus gene and the like.

In addition, the present invention provides a plant transformant transformed with the recombinant expression vector containing the constitutive promoter of plant. Particularly, the plant transformed with the recombinant expression vector pBGWFS7-PAtLip3 containing the constitutive promoter of SEQ. ID. NO: 1 is provided. The plant may include *Arabidopsis*, root crops such as carrot, sweet potato and radish, medicinal plant such as ginseng and *Codonopsis lanceolata*, fodder crops such as corn, and grain crops such as rice plant. Furthermore, the plant may include various kinds of dicotyledons.

In addition, the present invention provides seeds obtained from the plant transformed with the recombinant expression vector containing the constitutive promoter. The plant may include *Arabidopsis*, rootcrops such as carrot, sweet potato and radish, medicinal plant such as ginseng and *Codonopsis*

*lanceolata*, fodder crops such as corn, and grain crops such as rice plant. Furthermore, the plant may include various kinds of dicotyledons.

In addition, the present invention provides a method for expressing a target foreign protein constitutively within a plant, which comprises steps: (1) constructing a plant expression vector expressing an exogenous gene by using the constitutive promoter; (2) transforming a plant vehicle with the plant expression vector; and (3) introducing the plant vehicle into a plant to express the exogenous gene.

The exogenous gene capable of being expressed by the constitutive promoter may be all plant genes, but include one or more herbicide resistance genes, selective marker genes and/or reporter genes. It may include any useful genes improving genetic traits in a food plant and further, be applied to various researches upon comparing the capacity of promoters and the like.

EXAMPLES

Practical and presently preferred embodiments of the present invention are illustrated as shown in the following Examples.

However, it will be appreciated that those skilled in the art, on consideration of this disclosure, may make modifications and improvements within the spirit and scope of the present invention.

General experimental procedures not described clearly in following Examples should be referred to "Molecular Cloning" (Sambrook et al., A Laboratory Manual, Cold Spring Harbor Laboratory Press, Second Edition, 1989).

Example 1

Analysis of Expression Pattern of Putative Lipase Gene Derived from *Arabidopsis*

In order to examine the expression pattern of putative lipase genes derived from *Arabidopsis*, total RNAs was separated from roots, leaves, stalks, flowers and pods including growing seeds and analyzed by performing reverse transcriptase—polymerase chain reaction (RT-PCR). This process for isolating total RNA will be described more clearly as follows. Approximately 1 g of each sample was sonicated with a mixing bowl and transferred into a 1.5 ml tube. Then, 500 μl of RNA extraction buffer (50 mM sodium acetate (pH 5.5), 150 mM LiCl, 5 mM EDTA, 0.5% SDS) and 500 μl of phenol were added and blended in each tube. This mixture was reacted at 65° C. for 10 minutes in a rotary shaker for 15 minutes and centrifuged at 4° C. at 10,000 rpm for 10 minutes. The resulting supernatant layer was poured carefully into a fresh tube and mixed well with 500 μl of chloroform. Then, it was centrifuged again to collect supernatant. After that, 0.6 volume of 8 M lithium chloride (LiCl) was added and stored at 20° C. for more than 2 hours. Then, the resultant was centrifuged again at 4° C. at 12,000 rpm for 20 minutes. The final RNA pellet was washed respectively with 4 M LiCl and 80% ethanol and dissolved in 50 μl of distilled water.

The resulting RNA eluant was quantitated by measuring optical density at 260/280 nm with a UV spectrophotometer. Five μg of the total RNA for template was treated at 50° C. for 50 minutes and at 85° C. for 5 minutes with 50 μM oligo dT primers and cooled in ice. After that, 1 μl of RNase H was added and treated at 37° C. for 20 minutes so as to synthesize cDNAs (10×RT buffer, 25 mM $MgCl_2$, 0.1 M DTT, RNase OUT, SuperScript™ RT). The resulting cDNAs were used as template and reacted by performing PCR with an AtLip3 primer set specific for the lipase gene, Lip3-F primer of SEQ. ID. NO: 2 and Lip3-R primer of SEQ. ID. NO: 3. In order to adapt the relative amount of RNAs, a primer set specific for the elongation factor 1α gene of *Arabidopsis*, EF1α-F primer of SEQ. ID. NO: 4 and EF1α-R primer of SEQ. ID. NO: 5, was also used to conduct the PCR. The serial RT-PCR was performed under a following condition: denaturing at 95° C. for 7 minutes; 95° C. for 30 seconds; annealing at 60° C. for 30 seconds; 72° C. for 30 seconds repeatedly for 40 cycles; and then, reacting at 72° C. for 7 minutes.

As a result, it is identified that transcripts of the lipase gene derived from *Arabidopsis* were detected in all the tissues of leaves, stalks, flowers and cods including seeds and expressed constitutively. In this case, the relative amount of RNA was adjusted by using the primer set specific for the elongation factor 1a of *Arabidopsis*.

Figure 1:
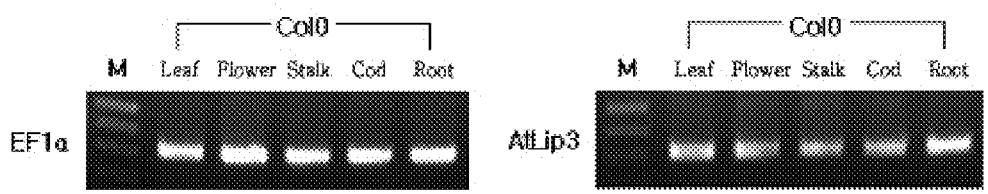
FIG. 1 depicts the AtLip3 promoter gene of the present invention that is amplified by using total RNAs with specific primers after being separated respectively from root, leaf, stem, flower and silique tissues of *Arabidopsis*, compared with a positive control group.

FIG. 1 depicts the AtLip3 promoter gene of the present invention that is amplified by using total RNA with specific primers after being separated respectively from root, leaf, stem, flower and silique tissues of *Arabidopsis*, compared with a positive control group. In this moment, M is 1 Kb plus DNA ladder marker; AtLip3, lipase gene of *Arabidopsis*; Co10: non-transformed *Arabidopsis*; and EF1α, elongation factor 1α gene of *Arabidopsis*.

Example 2

Construction of Plant Expression Vector Containing Lip3 Promoter of Lipase Gene

The expression pattern according to various tissues of *Arabidopsis* was examined by the procedure as described in the Example 1. Lipase genes corresponding to a constitutively expressed protein were screened by using total nucleotide sequences already disclosed in *Arabidopsis*. Also, approximately 1.98 kb region (SEQ. ID. NO: 1) upstream of a start codon of the lipase gene including TATA box and the like was separated. Then, it was manipulated to construct a recombinant vehicle for analyzing the function of the PAtLip3 promoter by using the Gateway vector pBGWFS7 (purchased from Gent University, Belgium). A small amount of leaf tissue prepared from the transformed *Arabidopsis* was added into an Eppendorf tube and purified by using Genomic DNA Purification Kit (I. J. BIO DNA System). The resulting DNA eluant was quantitated by measuring $A_{260}/A_{280}$ with a UV spectrophotometer. In order to specifically amplify PAtLip3 sequence from the genomic DNA of *Arabidopsis* that may include a part of recombinant sequences specific for bacteria when the bacteria be infected by bacteriophage, a primer set of SEQ. ID. NO: 6 and SEQ. ID. NO: 7 (PLip3-B1 primer and PLip3-B2 primer) was constructed as described in following Table 1. Then, PCR (polymerase chain reaction) was performed to separate about 1.98 kb promoter region by using the primer set.

TABLE 1

| Primer | Nucleotide sequences |
|---|---|
| PLip3-B1 | 5'-AAAAAGCAGGCTTAAGGAAGTTGAAGAGCTGG-3' |
| PLip3-B2 | 5'-AGAAAGCTGGGTAGAGAGCTGAAGGTTGGTCT-3' |
| PLip3-B1 | 5'-AAAAAGCAGGCTTAAGGAAGTTGAAGAGCTGG-3' |
| PLip3-B2 | 5'-AGAAAGCTGGGTAGAGAGCTGAAGGTTGGTCT-3' |

In order to compare a promoter activity of the PAtLip3 region with P35S promoter commonly used for transforming a dicotyledon plant, a primer set of SEQ. ID. NO: 8 and SEQ. ID. NO: 9 (35S-F primer and 35S-R primer) that is designed to amplify the P35S promoter including a part of bacteria-specific nucleotide sequences, was constructed to separate the P35S region. After that, the PCR product amplified above was amplified again by performing a PCR by using a primer set of SEQ. ID. NO: 10 and SEQ. ID. NO: 11 (B1 adapter primer and B2 adapter primer) that may include whole nucleotide sequences specific for bacteria when the bacteria be infected by bacteriophage.

In addition, the PCR product amplified secondarily was introduced into the cloning vector pDONR221 that may include nucleotide sequences specific for bacteriophage infection by using a BP recombination. Then, it was constructed to the recombinant cloning vector pDONR-PAtLip3 and pDONR-P35S. In order to complete vectors for plant transformation, 2 kinds of the vectors sub-cloned above were finally constructed to the recombinant expression vectors pBGWFS7-PAtLip3 and pBGWFS7-P35S through an LR recombination. In this procedure, the plant expression vector pBGWFS7 containing an intrinsic reporter system connecting Egfp gene and Gus gene was utilized as a binary vector. It also includes a spectinomycin resistance gene for microbial selection and an herbicide resistance gene Bar for plant selection. The recombinant vectors manufactured above were transformed into *Agrobacterium tumefaciens* GV3101 strain by performing a Agrobacteria transformation with liquid nitrogen (Holster et al., Freeze-thaw method, 1978). Then, they were introduced? into the *Agrobacterium* by using Agrobacteria quick-screen based upon alkaline lysis.

FIG. 2 depicts a construction map of the plant expression vector pBGWFS7-PAtLip3. In this moment, LB is left border; Tnos, nos terminator; BAR, herbicide resistance gene; Pnos, nos promoter; PAtLip3, lipase promoter; P35S, Cauliflower mosaic virus 35S promoter; Egfp, green fluorescent protein gene; GUS, blue-coloring β-glucuronidase gene; T35S, Cauliflower mosaic virus 35S terminator; and RB, right border.

Example 3

Transformation and Cultivation of *Arabidopsis* Plant

*Arabidopsis* plants were transformed with the expression vectors for plant transformation constructed in the Example 2 by a following procedure. Above all, *Arabidopsis thaliana* ecotype Columbia was seeded and cultured at 22° C. (for 16 hours day/8 hours night) during approximately 4 weeks. Then, primary sprouts were removed and minimal 3 to 4 sprouts were generated secondarily. After that, culture solution including Agrobacteria transformed with the recombinant vector for plant transformation was diluted to reach approximately OD 0.8 by using solution containing 0.5% sucrose and 2,500 ppm Tween 20. The resulting cell suspension was sprayed onto flower buds to infect the Agrobacteria. The infected Agrobacteria were cultivated overnight under a dark condition, while maintaining a sufficient humidity. Then, they were cultivated further for 4 to 5 days with an incubator at 22° C. (for 16 hours day/8 hours night). After that, the resulting *Agrobacteria* were sprayed onto flower buds again after being cultured and diluted by the same procedure. Afterward, they were cultivated overnight while maintaining a sufficient humidity under a dark condition. Further, they were cultivated for approximately 3 to 5 weeks in an incubator at 22° C. (for 16 hours day/8 hours night) until silique tissue became completely matured and brown colored and then, seeds were gathered. The seeds were sown again and sprayed with 0.3% BASTA at 10 days primarily and at 17 days secondarily so as to select T1 generation transformants. The resulting T1 transformed plant was cultivated for approximately 2 months with an incubator at 22° C. (for 16 hours day/8 hours night) until silique tissue became completely matured and brown colored and then, T2 seeds were gathered.

Example 4

Histochemical Staining of Gus Activity of Transgenic *Arabidopsis* Plant

The constitutive gene expression of *Arabidopsis* transformed above was examined by using a GUS staining through a following procedure. Above all, the T2 seeds transformed with the PAtLip3 promoter of the present invention and the P35S promoter were sown, cultivated and sprayed with 0.3% BASTA at 10 days primarily and at 17 days secondarily. The resulting *Arabidopsis* plant transformed above was examined to observe GUS staining according to growth stage in various tissues including leaf, stem, root, flower, silique etc. For a control group, a non-transformed *Arabidopsis* plant was germinated without treating BASTA. The transgenic *Arabidopsis* plants were soaked in GUS assay buffer [Sol I: X-gluc (cyclohexyl ammonium salt) 20 mM; Sol II: $NaH_2PO_4$ $H_2O$ 100 mM, NaEDTA 10 mM, Triton-X100 0.1%, pH 7.5] and treated at 37° C. for 24 hours after seeding at 7 days, 21 days and 42 days. Then, 70% ethanol was treated to remove chlorophylls. The resulting plant was observed by using a light microscope.

As a consequence, the P35S promoter transformant and the PAtLip3 promoter transformant were observed to appear GUS staining in whole bodies from 7-day-old seedlings. In contrast, the non-transformed *Arabidopsis* did not appear GUS staining at all. Even 21-day-old seedlings and 42-day-old plants, the non-transformed *Arabidopsis* did not appear GUS staining at all, but the P35S transformant and the PAtLip3 transformant were detected to appear GUS staining in whole bodies. Therefore, it is confirmed that the PAtLip3 promoter should be a constitutive promoter as the P35S promoter is.

FIG. 4 depicts the *Arabidopsis* transformed with the plant expression vector pBGWFS7-PAtLip3 that appears histochemical staining of GUS activity during seedlings to maturing plants. At this moment, Col10 is non-transformed *Arabidopsis*; P35S::GUS, transformed *Arabidopsis* as a control group; PAtLip3::GUS:, *Arabidopsis* transformed with the plant expression vector pBGWFS7-PAtLip3; 7D, 7-day-old-seedlings; 21D, 21-day-old-seedlings; and 42D, 42-day-old plant.

Example 5

Quantitation of the Gus Enzyme Activity Of Transgenic *Arabidopsis*

The constitutive expression of *Arabidopsis* transformed above was quantitated by using a fluorometric GUS assay through a following procedure. Above all in order to measure a degree of GUS enzyme activity from the PAtLip3 promoter of the present invention, total proteins were separated from leaves, roots, stalks, cods and flowers in 2 kinds of T2 generation *Arabidopsis* transformed with the PAtLip3 promoter and the *Arabidopsis* transformed with the P35S promoter and non-transformed *Arabidopsis* respectively. Tissue samples were sonicated with a mixing bowl by using liquid nitrogen. About 50 mg of each sample was transferred into a 1.5 ml tube and mixed vigorously with 100 µl of protein extraction buffer [50 mM sodium phosphate (pH 7.0), 10 mM dithiothreitol (DTT), 1 mM disodium EDTA, 0.1% SDS, 0.1% Triton X-100] The resulting mixture was centrifuged at 4° C. at 15,000 rpm for 5 minutes. The resulting supernatant was collected into a fresh tube. Then, 50 µl of the supernatant was mixed with 50 µl of assay buffer (1.2 mM MUGlu, 10.0 mM β-mercaptoethanol in 1× reaction buffer; FluorAce β-glucuronidase reporter assay kit, Bio-Rad) after being adjusted at 37° C. and reacted with a water bath at 37° C. for 30 minutes. Further, the resultant of each sample was mixed well with 100 µl of 1× stopping buffer and analyzed with a fluorescence spectrometer (excitation filter 355 nm, emission filter 460 nm) to measure its GUS activity. FIG. 5 depicts a quantitative assay of GUS enzyme activity that is expressed from the AtLip3 promoter of the present invention, compared with a positive control group. As a consequence, it is confirmed that the PAtLip3 promoter should be a constitutive promoter capable of expressing foreign genes to almost the same or increasing levels more than the P35S promoter.

Example 6

Examination of Constitutive Expression in Transgenic *Arabidopsis* Plant by Performing RT-PCR The constitutive expression of *Arabidopsis* transformed above was examined by performing a reverse transcriptase-polymerase chain reaction through a following procedure. Above all T2 seed transformed above were sown and sprayed with 0.3% BASTA at 10 days after being cultured primarily and at 17 days secondarily. Then, various tissues such as leaf, stem, root, flower and silique (including 3-weeked seeds after being bloomed were collected from the *Arabidopsis* plant transformed above. After that, through the same procedure described in the Example 1, 10 µg of total RNA extracted was used as template and treated at 50° C. for 50 minutes and at 85° C. for 5 minutes with 50 µM oligo dT primers and cooled in ice. Then, 1 µl of RNase H was added again and treated at 37° C. for 20 minutes so as to synthesize cDNAs (10×RT buffer, 25 mM MgCl$_2$, 0.1 M DTT, RNase OUT, SuperScript™ RT). The resulting cDNAs was used as template and reacted by performing a PCR with a GUS primer set specific for Blue-coloring gene, GUS-F primer of SEQ. ID. NO: 12 and GUS-R primer of SEQ. ID. NO: 13. In order to adapt the relative amount of RNAs, a primer set specific for the elongation factor 1α gene of *Arabidopsis*, EF1α-F primer of SEQ. ID. NO: 4 and EF1α-R primer of SEQ. ID. NO: 5 was also used to conduct the PCR. The serial RT-PCR was performed under a following condition: denaturing at 95° C. for 7 minutes; 95° C. for 30 seconds; annealing at 60° C. for 30 seconds; 72° C. for 30 seconds repeatedly for 40 cycles; and then, reacting at 72° C. for 7 minutes.

As a result, it is identified that transcripts of the GUS gene were detected in all the tissues of leaves, stems, flowers and siliques including seeds from *Arabidopsis* plants transformed with the PAtLip3 promoter and expressed constitutively. In this case, the relative amount of RNA was adjusted by using the primer set specific for the elongation factor 1α of *Arabidopsis*.

FIG. 6 depicts the promoter gene of the present invention that is amplified by using total RNAs with specific primers after being separated respectively from root, leaf, stem, flower and seed tissues of *Arabidopsis* plants transformed with the plant expression vector pBGWFS7-PAtLip3, compared with a positive control group and GUS gene. At this moment, M is 1 Kb plus DNA ladder marker; GUS, β-glucuronidase gene; EF1α, elongation factor 1α gene of *Arabidopsis*; 1, leaves of non-transformed *Arabidopsis*; 2, flowers of non-transformed *Arabidopsis*; 3, stems of non-transformed *Arabidopsis*; 4, seeds of non-transformed *Arabidopsis*; 5, roots of non-transformed *Arabidopsis*; 6, leaves of *Arabidopsis* transformed with PAtLip3 gene; 7, flowers of *Arabidopsis* transformed with PAtLip3 gene; 8, stem of *Arabidopsis* transformed with PAtLip3 gene; 9, seeds of *Arabidopsis* transformed with PAtLip3 gene; 10, roots of *Arabidopsis* transformed with PAtLip3 gene; 11, leaves of *Arabidopsis* transformed with P35S gene; 12, flowers of *Arabidopsis* transformed with P35S gene; 13, stem of *Arabidopsis* transformed with P35S gene; 14, seeds of *Arabidopsis* transformed with P35S gene; and 15, roots of *Arabidopsis* transformed with P35S gene.

As illustrated and confirmed above, the present invention relates to a novel constitutive promoter of plant, particularly to a lipase promoter Lip3 derived from *Arabidopsis*, a method for isolating the same, a recombinant expression vector containing the same and a use of the same for improving traits of a farm product. The constitutive promoter of the present invention can be utilized to induce a constitutive gene expression such as herbicide resistance gene and reporter gene, because it can express an exogenous gene regardless of its expression site. In addition, it can be applied widely in the future to develop a transformed plant improving its useful trait.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A recombinant expression vector comprising constitutive promoter Lip3 of plant having the nucleotide sequence of SEQ ID NO:1.

2. The recombinant expression vector according to claim 1, wherein the constitutive promoter Lip3 of plant is obtained from *Arabidopsis thaliana*.

3. The recombinant expression vector according to claim 1, which is the recombinant expression vector pBGWFS7-PatLip3 having accession number: KCTC 11522 BP.

4. A plant transformant transformed with the recombinant expression vector of claim 1.

5. A method for expressing an exogenous protein constitutively within a plant, which comprises the steps of: (1) constructing a plant expression vector expressing an exogenous gene by using the constitutive promoter according to claim 1; (2) transforming a plant vehicle with the plant expression vector; and (3) introducing the plant vehicle into the plant to express the exogenous protein.

* * * * *